US009412559B2

(12) United States Patent
Tanner

(10) Patent No.: US 9,412,559 B2
(45) Date of Patent: *Aug. 9, 2016

(54) AUTOMATED SLICE MILLING FOR VIEWING A FEATURE

(71) Applicant: FEI Company, Hillsboro, OR (US)

(72) Inventor: Ryan Tanner, Beaverton, OR (US)

(73) Assignee: FEI COMPANY, Hillsboro, OR (US)

( * ) Notice: Subject to any disclaimer, the term of this patent is extended or adjusted under 35 U.S.C. 154(b) by 81 days.

This patent is subject to a terminal disclaimer.

(21) Appl. No.: 14/311,614

(22) Filed: Jun. 23, 2014

(65) Prior Publication Data

US 2015/0021475 A1  Jan. 22, 2015

Related U.S. Application Data

(63) Continuation of application No. 13/735,714, filed on Jan. 7, 2013, now Pat. No. 8,759,802, which is a continuation of application No. 12/751,496, filed on Mar. 31, 2010, now Pat. No. 8,350,237.

(51) Int. Cl.
*H01J 37/304* (2006.01)
*H01J 37/30* (2006.01)
(Continued)

(52) U.S. Cl.
CPC ............ *H01J 37/3005* (2013.01); *G01N 1/286* (2013.01); *H01J 37/26* (2013.01);
(Continued)

(58) Field of Classification Search
CPC ..... H01J 37/3005; H01J 37/26; H01J 37/265; H01J 37/28; H01J 37/30; H01J 37/3045; H01J 37/3056; H01J 2237/2611; H01J 2237/28; H01J 2237/2803; H01J 2237/2814; H01J 2237/30472; H01J 2237/3174; H01J 2237/31745; H01J 2237/31749
See application file for complete search history.

(56) References Cited

U.S. PATENT DOCUMENTS

| 5,435,850 A | 7/1995 | Rasmussen |
| 5,698,397 A | 12/1997 | Zarling et al. |

(Continued)

FOREIGN PATENT DOCUMENTS

| EP | 2149897 A1 | 2/2010 |
| JP | H08115699 | 5/1996 |

(Continued)

OTHER PUBLICATIONS

Ewald, Andrew J., et al., 'Surface Imaging Microscopy, An Automated Method for Visualizing Whole Embryo Samples in Three Dimensions at High Resolution,' Developmental Dynamics, 2002, pp. 369-375, vol. 225.

(Continued)

*Primary Examiner* — Jack Berman
(74) *Attorney, Agent, or Firm* — Michael O. Scheinberg; Scheinberg & Associate

(57) ABSTRACT

A method and apparatus for performing a slice and view technique with a dual beam system. The feature of interest in an image of a sample is located by machine vision, and the area to be milled and imaged in a subsequent slice and view iteration is determined through analysis of data gathered by the machine vision at least in part. A determined milling area may be represented as a bounding box around a feature, which dimensions can be changed in accordance with the analysis step. The FIB is then adjusted accordingly to slice and mill a new face in the subsequent slice and view iteration, and the SEM images the new face. Because the present invention accurately locates the feature and determines an appropriate size of area to mill and image, efficiency is increased by preventing the unnecessary milling of substrate that does not contain the feature of interest.

21 Claims, 8 Drawing Sheets

(51) Int. Cl.
*H01J 37/28* (2006.01)
*H01J 37/305* (2006.01)
*H01J 37/26* (2006.01)
*G01N 1/28* (2006.01)

(52) U.S. Cl.
CPC .............. *H01J 37/265* (2013.01); *H01J 37/28* (2013.01); *H01J 37/30* (2013.01); *H01J 37/3045* (2013.01); *H01J 37/3056* (2013.01); *H01J 2237/2611* (2013.01); *H01J 2237/28* (2013.01); *H01J 2237/2803* (2013.01); *H01J 2237/2814* (2013.01); *H01J 2237/30472* (2013.01); *H01J 2237/3174* (2013.01); *H01J 2237/31745* (2013.01); *H01J 2237/31749* (2013.01)

(56) References Cited

U.S. PATENT DOCUMENTS

| | | | |
|---|---|---|---|
| 5,851,413 | A | 12/1998 | Casella et al. |
| 6,518,571 | B2 | 2/2003 | Talbot et al. |
| 6,546,788 | B2 | 4/2003 | Magerle |
| 6,839,470 | B2 | 1/2005 | Ikeda |
| 6,888,136 | B2 | 5/2005 | Geurts et al. |
| 6,889,113 | B2 | 5/2005 | Tasker et al. |
| 6,909,791 | B2 | 6/2005 | Nikitin et al. |
| 6,955,078 | B2 | 10/2005 | Mancevski et al. |
| 7,103,505 | B2 | 9/2006 | Teshima et al. |
| 7,135,123 | B1 | 11/2006 | Thompson et al. |
| 7,230,243 | B2 | 6/2007 | Tanaka et al. |
| 7,312,448 | B2 | 12/2007 | Principe |
| 7,317,515 | B2 | 1/2008 | Buijsse et al. |
| 7,348,556 | B2 | 3/2008 | Chitturi et al. |
| 7,365,325 | B2 | 4/2008 | Miyamoto et al. |
| 7,474,986 | B2 | 1/2009 | Teshima et al. |
| 8,306,264 | B2 | 11/2012 | Fujii et al. |
| 8,350,237 | B2 * | 1/2013 | Tanner .................. G01N 1/286 250/307 |
| 8,455,824 | B2 | 6/2013 | Muto et al. |
| 8,759,802 | B2 * | 6/2014 | Tanner .................. G01N 1/286 250/307 |
| 2004/0140438 | A1 | 7/2004 | Gerlach et al. |
| 2006/0192118 | A1 | 8/2006 | Tashiro et al. |
| 2007/0018099 | A1 | 1/2007 | Chitturi et al. |
| 2008/0042059 | A1 | 2/2008 | Tashiro et al. |
| 2008/0088831 | A1 | 4/2008 | Mulders et al. |
| 2008/0142735 | A1 | 6/2008 | Chandler et al. |
| 2009/0220130 | A1 | 9/2009 | Slingerland |
| 2009/0242759 | A1 | 10/2009 | Bray et al. |
| 2010/0092070 | A1 | 4/2010 | Young et al. |
| 2010/0108506 | A1 | 5/2010 | Nadeau et al. |
| 2012/0056088 | A1 | 3/2012 | Rue |

FOREIGN PATENT DOCUMENTS

| | | |
|---|---|---|
| JP | H11273613 | 10/1999 |
| JP | 2004061376 A | 2/2004 |
| JP | 2004191358 A | 7/2004 |
| JP | 2005122909 A | 5/2005 |
| JP | 2006221961 A | 8/2006 |
| JP | 2007184175 A | 7/2007 |
| JP | 2010002314 A | 1/2010 |
| JP | 2011185845 A | 9/2011 |
| WO | WO9740493 A1 | 10/1997 |

OTHER PUBLICATIONS

Frank, Joachim, "Electron Tomography: Three-Dimensional Imaging with the Transmission Electron Microscope," 1992, pp. 1-13.
Gonzalez-Melendi, Pablo, et al., "3-D Gold In Situ Labelling in the EM," The Planet Journal, 2002, pp. 237-243, vol. 29, Iss. 2.
Holzer, L., et al., 'Three-Dimensional Analysis of Porous BaTiO3 Ceramics Using FIB Nanotomography,' Journal of Microscopy, Oct. 2004, pp. 84-95, vol. 216, Pt. 1.
Nagato, Yasukazu, et al., 'Observation on Backscattered Electron Image (BEI) of a Scanning Electron Microscope (SEM) in Semi-thin Sections Prepared for Light Microscopy,' Tokai J. Exp. Clin. Med., 1983, pp. 167-174, vol. 8, No. 2.
Steer, T.J., et al., "3-D Focused Ion Beam Mapping of Nanoindentation Zones in a Cu—Ti Multilayered Coating," Thin Solid Films, 2002, pp. 147-154, vol. 413.
Harrison, Christopher, et al., "Layer by Layer Imaging of Diblock Copolymer Films with a Scanning Electron Microscope," Polymer, 1998, pp. 2733-2744, vol. 39, Iss. 13.
Heymann, Jurgen A.W., et al., "Site-Specific 3D Imaging of Cells and Tissues with a Dual Beam Microscope," Journal of Structural Biology, 2006, pp. 63-73, vol. 155.
Scott, John E., et al., 'Dermatan sulphate-rich proteoglycan associates with rat tail-tendon collagen at the d band in the gap region,' Biochem. J., 1981, pp. 213-216, vol. 197.
Shimizu, Daisaburo, et al., "Three-Dimensional Reconstruction by Scanning Electron Microscopy from Serial Epoxy Resin Semi-Thin Sections After Ion-Etching," Journal of Electron Microscopy, 2001, pp. 51-55, vol. 50, Iss. 1.
Thiberge, Stephan, et al., "Scanning Electron Microscopy of Cells and Tissues under Fully Hydrated Conditions," Proceedings of the National Academy of Sciences, Mar. 9, 2004, pp. 3346-3351, vol. 101, Iss. 10.
Weninger, Wolfgang Johann, et al., "Phenotyping Transgenic Embryos: a Rapid 3-D Screening Method Based on Episcopic Fluorescence Image Capturing," Nature Genetics, Jan. 2002, 7 pgs, vol. 30.
Drobne, Damjana et al., "Focused Ion Beam/Scanning Electron Microscopy Studies of Porcellio scaber (Isopoda, Crustacea) Digestive Gland Epithelium Cells," The Journal of Scanning Microscopies, Jan./Feb. 2005, pp. 30-34, vol. 27, Issue 1.
Giannuzzi, Lucille A., et al., "Site-Specific Cross-Sectioning" in Chapter 12 "Dual-Beam (FIB-SEM) Systems" in "Introduction to Focused Ion Beams," Springer, USA XP055015026, Jan. 1, 2004, pp. 240-255.
Zaefferer, S., et al., "Three-Dimensional Orientation Microscopy in a Focused Ion Beam-Scanning Electron Microscope: A New Dimension of Microstructure Characterization," Metallurgical and Materials Transactions, Feb. 2008, vol. 39A, pp. 374-389.

* cited by examiner

AUTOMATED SLICE MILLING FOR VIEWING A FEATURE

This application is a Continuation of U.S. application Ser. No. 12/751,496, filed Mar. 31, 2010, which is hereby incorporated by reference.

TECHNICAL FIELD OF THE INVENTION

The present invention generally relates to charged particle beam imaging for nanotechnology, and more particularly to a method for automatically locating a feature in a sample for slice milling and viewing.

BACKGROUND OF THE INVENTION

Electron microscopy offers the opportunity to study material architectures in 3D at high resolution. In the field of biological sciences, for example, electron microscopy allows the observation of molecular mechanisms of diseases, the conformation of flexible protein structures and the behavior of individual viruses and proteins in their natural biological context. One technique employed with electron microscopy for analyzing biological materials, for example, is called Slice-and-View™ (hereafter "slice and view"). This technique is typically performed with a dual beam system, that is, a system combining a focused ion beam (FIB) and a scanning electron microscope (SEM) such as the DualBeam® (hereafter "dual beam") instruments commercially available from FEI Company, the assignee of the present invention.

In the slice and view technique, the FIB cuts and slices a sample with high precision to reveal its 3D internal structures or features. Typically, the FIB exposes a cross section, or face, perpendicular to the top of the surface of the sample material having the hidden feature to be viewed. Because the SEM beam axis is typically at an acute angle relative to the FIB beam axis, a portion of the sample in front of the face is preferably removed so that the SEM beam can have access to image the face. After obtaining an image of the face by the SEM, another layer of substrate at the face may be removed using the FIB, revealing a new, deeper face and thus a deeper cross-section of the feature. Since only the portion of the feature at the very surface of the face is visible to the SEM, sequential repetition of cutting and imaging, or slicing and viewing, provides the data needed to reconstruct the sliced sample into a 3D representation of the feature. The 3D structure is then used to analyze the feature.

The processing of a sample through a slice and view procedure can take a long time if a large section of the sample is processed. This is also true even if the feature of interest is relatively small in relation to the sample because the location of the feature is not typically known with sufficient accuracy to direct the beams of the FIB and SEM to the immediate region of the sample containing the feature. Therefore, a large section of the sample suspected of having the feature is processed in order to locate the feature. With a typical maximum field of view for the SEM being about 150 microns, slice milling and imaging an area this size can be a significant time investment, especially with high resolution settings on the SEM. Alternatively, many smaller portions of the area may be imaged, but doing so generates a vast amount of image data, and the resulting images are typically required to be stitched together to form a larger composite image. Such processes currently can last anywhere from a few hours to several days.

In prior art methods a relatively large section has been required to be processed with every iteration of the slice and view procedure because the shape or direction of the feature through the sample has not been accurately predicted. This problem is especially exacerbated with certain features that have long, winding shapes through the sample, such as is the case with blood vessels or nerves.

In the interest of time, it would be more efficient to slice mill a relatively smaller amount of substrate material necessary to view the feature of interest. Further, it would be more efficient to image a relatively smaller portion of the substrate that contains the feature.

SUMMARY OF THE INVENTION

Embodiments of a method and apparatus are provided herein for processing features with a slice and view technique that requires less time to perform than prior art methods, and is therefore more efficient.

This invention comprises a method and apparatus for slice milling multiple sequential cuts progressing into the face of a cross section wall of a sample, wherein the cuts are made by removing a minimum amount of sample material necessary to reveal and image the feature. Some embodiments include automatically determining whether to change certain parameters of the beams after each iteration of the slice and view process, that is, as each slice reveals a change in location of the feature as it extends through the sample. To this end, machine vision is used to track and detect the center of mass of the feature and its edges to provide a boundary box around the feature that aids in determining whether, and by what extent, to change the parameters of the beams as they process the sample. Some embodiments provide for automatically determining if a feature divides, or branches, from one sliced face to the next and which branch to track. Also, some embodiments automatically remove sample material that occludes the SEM beam from having a direct line of sight to the slice milled face.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more through understanding of the present invention, and advantages thereof, reference is now made to the following descriptions taken in conjunction with the accompanying drawings, in which.

DETAILED DESCRIPTION OF PREFERRED EMBODIMENTS

Figure 1A:
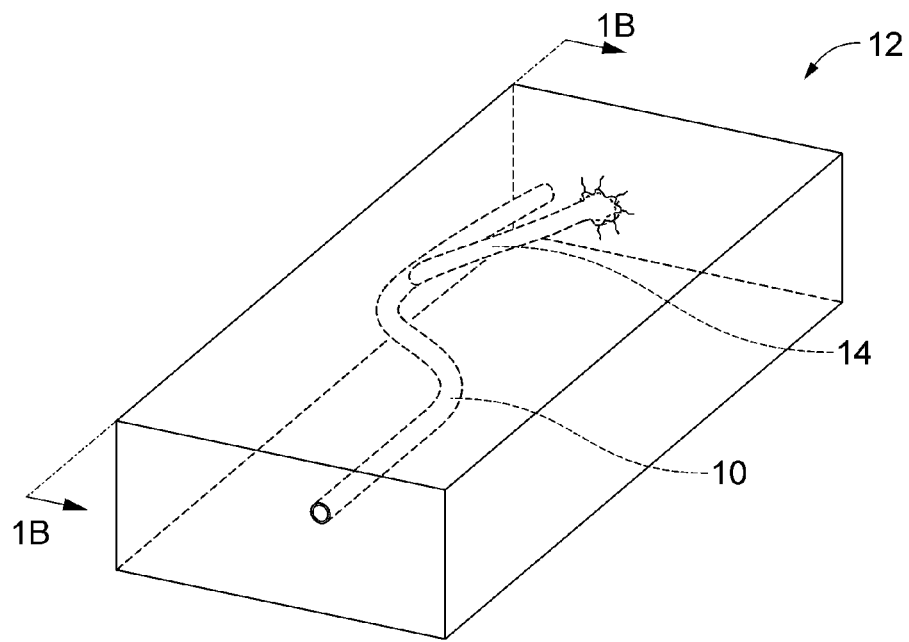
FIG. 1A shows a perspective view of a sample with a feature of interest having a non-linear path through the sample.

According to preferred embodiments of the present invention, a method and apparatus for processing a sample with a slice and view technique includes automatically locating and measuring a feature of interest in an image of a slice of the sample, predicting the location of the feature in a subsequent slice, and determining an area size to slice and image that includes the feature in the subsequent slice and view iteration. After determining the area to slice and image, the FIB and SEM are adjusted from the previous iteration to process the determined area in the subsequent iteration. By slicing and viewing only the areas sizes necessary for gathering the desired information about the feature of interest, the present invention provides for slicing and viewing a relatively smaller area of the sample than typically possible with prior art methods. Therefore, a sample can be processed much quicker.

Determining the size and shape of the sample material to mill includes observing the size and shape of the feature imaged from each iteration of the technique. Therefore, even if the size of the feature changes or the feature actually changes position or location to or from another side of the sample with respect to a previous image of the feature, the FIB and SEM are adjusted to process the feature with each iteration of the technique.

As used herein, the term "mill" generally means to remove material, and the term "slice" or "slice mill" means removing material in the shape of a slice. The term "slice" when used herein as a noun means the surface viewable after slice milling has been performed to remove material to expose that surface. The milled slices produced by the FIB milling process are typically between 20 nm-100 nm, but may be up to 500 nm depending on application. It is preferable, however, that slice thickness is between about 30 nm and about 60 nm, more preferably between about 35 nm and about 45 nm, and most preferably between about 35 nm and about 40 nm. In one embodiment, applicants found that a slice thickness of about 38 nm is sufficient to capture an image of relative small features while still providing an image having good contrast. It is also preferable that each slice be one or two pixels thick in an image, depending on the size of the field of view. The slices are preferably produced by a "line mill" rather than a "bulk mill," that is, by milling essentially a one dimensional line rather than a rectangle. Slices between 10 μm-100 μm in the X or Y dimensions, that is, width and height, are preferable. This area may be represented as a "bounding box" on an image of a sample. An "image" as used herein means an image displayed on a display unit or on a disposable medium such as paper, as well as a representation thereof in a computer memory, for example.

FIB operating currents for preferred embodiments are between 100 pA-1 nA at voltages around at 30 kV for all slicing and preparation steps, although a skilled artisan will appreciate that beam diameter and beam current are typically system specific. Beam chemistry may also be used in conjunction with the FIB or SEM processes. For milling with the FIB, a selective carbon etch or an insulator enhanced etch may be preferred. For surface preservation, platinum, carbon, or tungsten may be applied to areas desired to be protected during the milling steps.

The SEM electron beam is typically operated at a voltage of 5 kV and may preferably use a through-the-lens detector. It should be appreciated that, as in the case of the FIB described above, the operating parameters of the SEM vary depending on the materials imaged and should be optimized for each use without undue experimentation. For example, SEM beam voltages are preferably set anywhere from 500V-up to 30 kV.

Figure 1B:
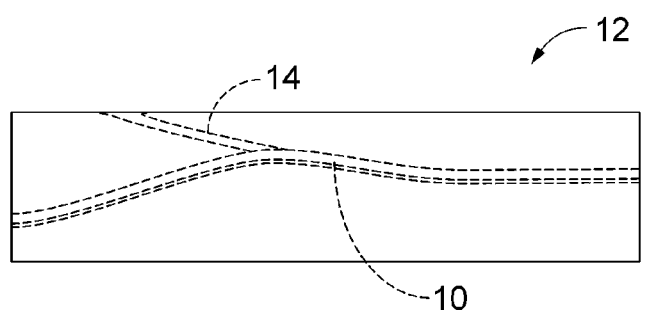
FIG. 1B shows the sample through line "1B" of FIG. 1A.
Figure 2:
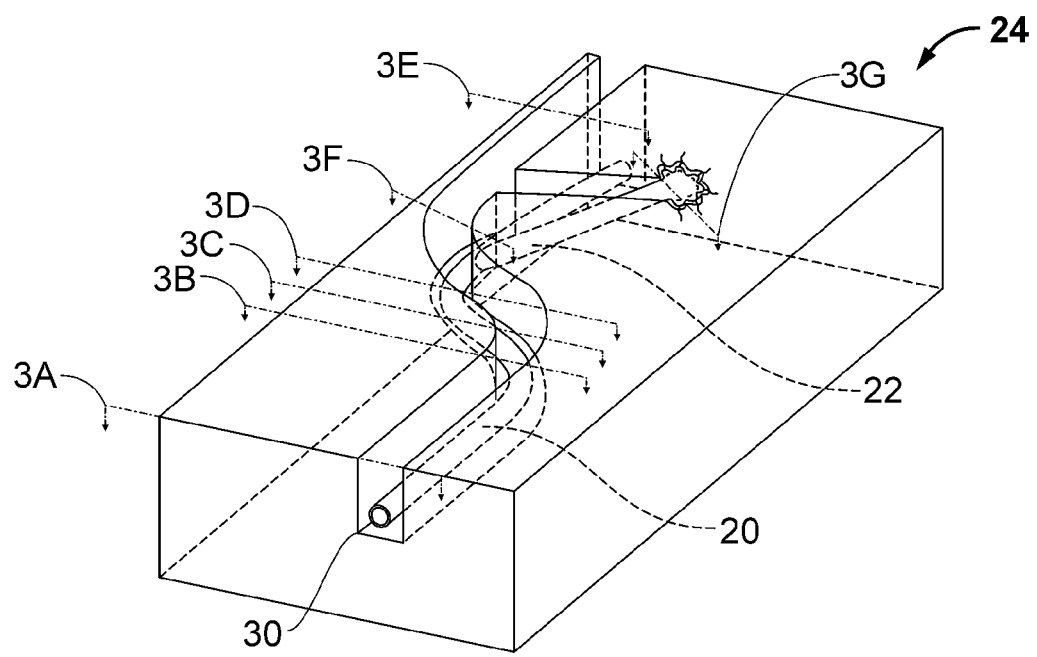
FIG. 2 shows a perspective view of a sample with a feature of interest having a non-linear path through the sample with reference locations for later discussion.

Although the objects most advantageously observed with the present invention are typically biological structures (e.g. nerves, blood vessels, cellular structures, etc.), it should be understood that the present invention is not limited to those materials and may include other materials such as metals, catalysts, polymers, and semiconductor circuits, for example. Feature of interest 10 of FIGS. 1A and 1B is illustrative of a biological structure that has a non-uniform shape through a sample 12, and may also have a branched member 14.

It is preferable for accuracy and automation that the size and shape of the area to be milled is determined through information gathered by machine vision. Machine vision is known in the art. In machine vision, a computer is used to process image information, usually obtained from the SEM image, to determine physical properties of a feature such as a feature's edges, size, and center of mass. Software used for machine vision may include, for example, Cognex VisionPro software from Cognex Corporation, Nantick, Mass. Typical machine vision software operates to identify a feature in a sample region based on image properties such as average gray level, contrast and texture. For instance, each pixel in the image may be given an assigned value, such as a single number, that represents a texture quality of that pixel with respect to surrounding pixels. The feature of interest will typically have different image properties, such as texture, from the surrounding sample in which the feature is imaged. The feature of interest therefore can be identified as the group of pixels having an average texture within a certain parameter of value that differs from the surrounding image. The machine vision software preferably automatically locates and measures the feature of interest in each imaged slice of the sample. FIGS. 3A-3G show different slices of feature 20 and branch 22 taken at various depths within the sample 24.

Figure 3A:
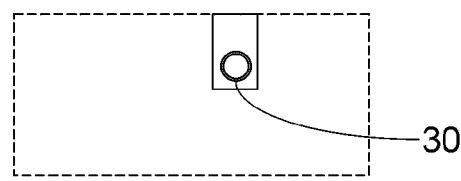
FIGS. 3A through 3G show various cross sectional views of the sample of FIG. 2.

Once the feature is located and measurements are obtained, computer software predicts, based on those measurements, the size of an area to mill slice in the next iteration of the slice and view process. For example, feature 30 as illustrated in FIG. 3A appears to be perfectly circular, suggesting that the position of the feature in the next slice would be in the same location as feature 30. In this case, slicing and viewing processes would follow the feature structure by continuing in a straight line direction into the sample if no changes in feature shape and size are revealed.

In determining the area to be milled in a subsequent slice milling step, it is first determined if the imaged feature as compared to a previously imaged slice of the feature has changed size or shape, which may indicate a change in feature position for the subsequent slices. For example, a deviation from the normal axial cross-section of a tubular-shaped feature tends to indicate that in a subsequent slice, the position of the feature may change from the previous slice. If such a change is indicated, the FIB and SEM beams would be adjusted to "follow" the feature as it changes size, shape or location.

To further illustrate this point, if an image of a tubular feature such as a blood vessel or nerve is shown as round, it is likely that the cross-section is substantially perpendicular to the longitudinal axis of the feature in that slice and that the feature is likely to extend through the sample, at least immediately, perpendicularly from the plane of the cut (sliced) face. A subsequent image showing a substantially round or circular feature would serve to confirm this determination. However, if a following image showed a feature with an elliptical shape, it would suggest that the feature does not extend perpendicularly from the cut face, but instead extends to a direction that can be determined by the orientation of the ellipse.

Figure 3B:
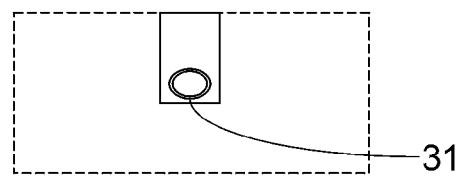
Figure 3C:
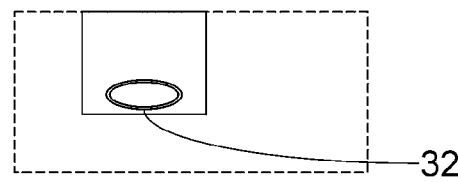
Figure 3D:
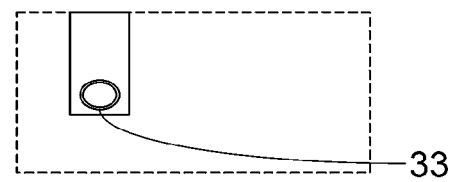
Figure 3E:
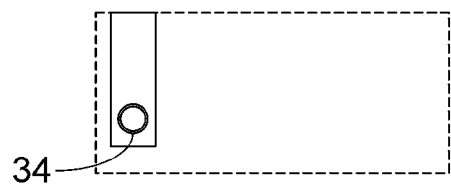

For example, the imaged slice of FIG. 3B shows that the shape of the feature 31 is slightly elliptical compared to feature 30. Here, at some point between the slices of FIG. 3A and 3B, it was determined that the feature shape was changing, indicating a subsequent change in location of the feature through continued processing. Feature 31 indicates that the feature is changing position toward the left of the sample (as shown on the page). FIG. 3C confirms that the feature has changed position far left. Also, the highly elliptical shape of feature 32 would also serve to indicate a greater change in location in the subsequent slice to be made that did the only slightly elliptical shape of feature 31. Here, a prediction may be made that a subsequent slice should be performed further to the left. FIG. 3D shows feature 33 further to the left, confirming the prediction of FIG. 3C. Feature 33, however, shows a less elliptical shape, indicating that the feature is "straightening out." FIG. 3E shows feature 34 near the end of the sample 24. Notice the change in location of the feature beginning from FIG. 3A to FIG. 3E.

Figure 3F:
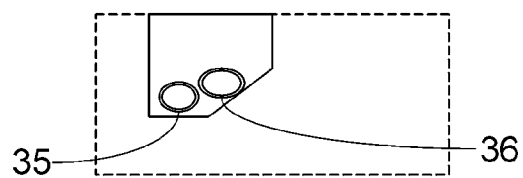
Figure 3G:
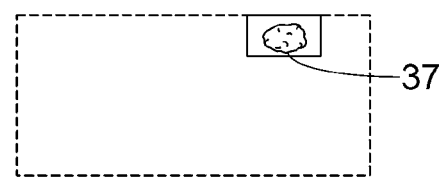

In at least one embodiment of the present invention, it may be desired to follow a branch of a structure. A branch may be imaged and located as shown in the slice of FIG. 3F, where feature 35 is the main structure and 36 is the branch. If the branch 36 is followed, it is shown to culminate at structure 37 shown in FIG. 3G.

It is preferable that a representative "bounding box" is assigned to that area on the image, shown in FIGS. 3A-3G as the solid-lined box around each feature. The bounding box includes the feature of interest and an area around the perimeter of the feature. The area around the perimeter of the feature is included to be milled to account for a margin of error in the predicting of the location, size and shape of the feature in the slice to be subsequently performed and for providing adequate sample area for the machine vision to compare the feature of interest with the surrounding sample material. The bounding box in each of FIGS. 3A-3G figure is much smaller than the dotted-lined box representing an area that would be milled in a typical prior art method.

Figure 4A:
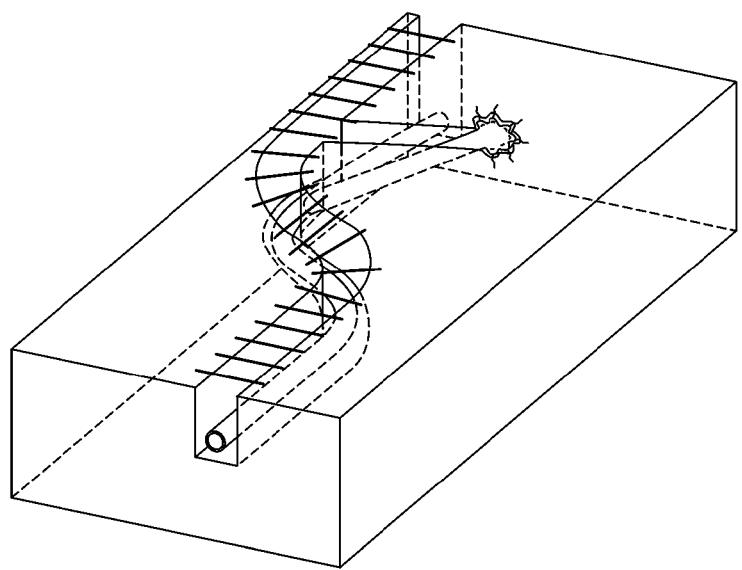
FIG. 4A shows an example of slices to be taken perpendicular to the longitudinal cross section of the feature of interest having a non-linear path through the sample.
Figure 4B:
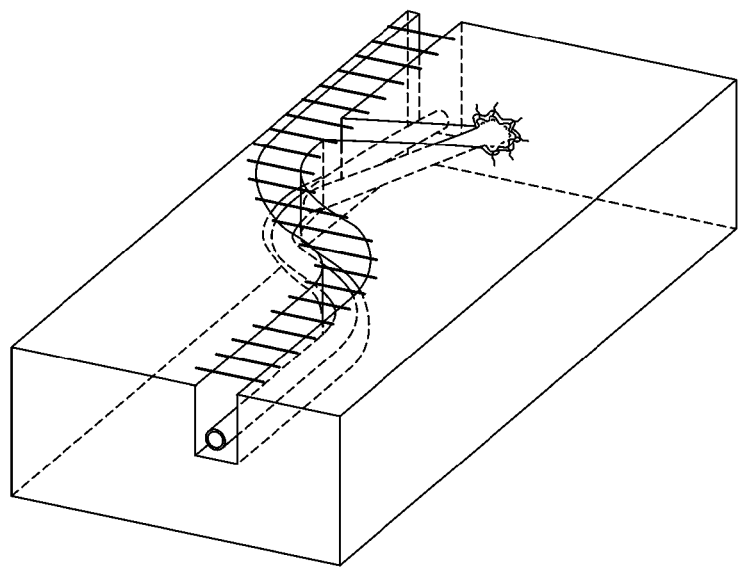
FIG. 4B shows an example of slices to be taken parallel to each other along the path of the feature of interest having a non-linear path through the sample.

The embodiments of the previous examples include slice milling (and imaging) parallel slices, as shown in FIG. 4B. However, other embodiments may include slice milling (and imaging) perpendicularly along the axial center of the feature as determined by the machine vision measurements of the feature. That is, as the imaged feature begins to show elliptical structure, the FIB and SEM (or stage having the sample) is moved accordingly to maintain the beams for processing perpendicularly axial slices along the body of the structure as shown in FIG. 4A. In other words, it may be preferable in at least some embodiments to image a new area by moving the sample rather than changing the beam parameters associated with that function, as is done in FIG. 4B. The sample may be moved, for example, by moving the stage or other apparatus such that the sample is moved in relation to the beams. It will be appreciated by one of ordinary skill in the art that the embodiment illustrated by FIG. 4A allows the tracking of features that move outside of the maximum field of view of the beams by repositioning the sample in relation to the beams.

Since the present invention provides for following the feature in a sample and milling less substrate material than in prior art methods, it is possible that un-milled substrate material may prevent obtaining an unobstructed image of the sliced face due to the orientation of typical dual-beam systems. The ion beam column of the FIB is typically oriented normal, or a few degrees from normal, to the sample surface, while the electron beam of the SEM is typically oriented at about 52 degrees with respect to the ion beam column. As processing of the sample is continued by slicing further into the sample, a substantial change of location of the feature may position the feature behind an obstruction of sample material preventing direct access by the SEM beam. To remedy this problem, embodiments of the present invention provide for obliterating the obstructing remnant of sample material.

Figure 5A:
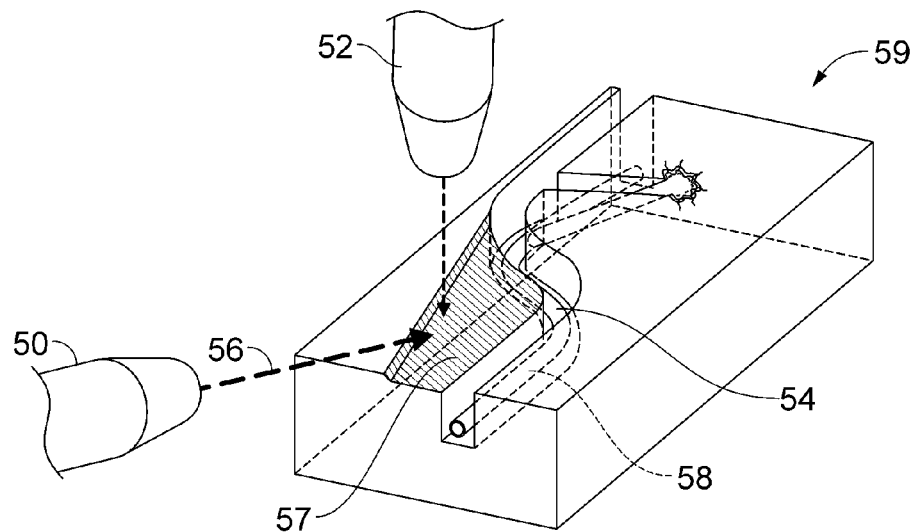
FIG. 5A shows the relationship of the FIB and SEM beams with respect to an obstruction area of the sample preventing imaging of the feature by the SEM.
Figure 5B:
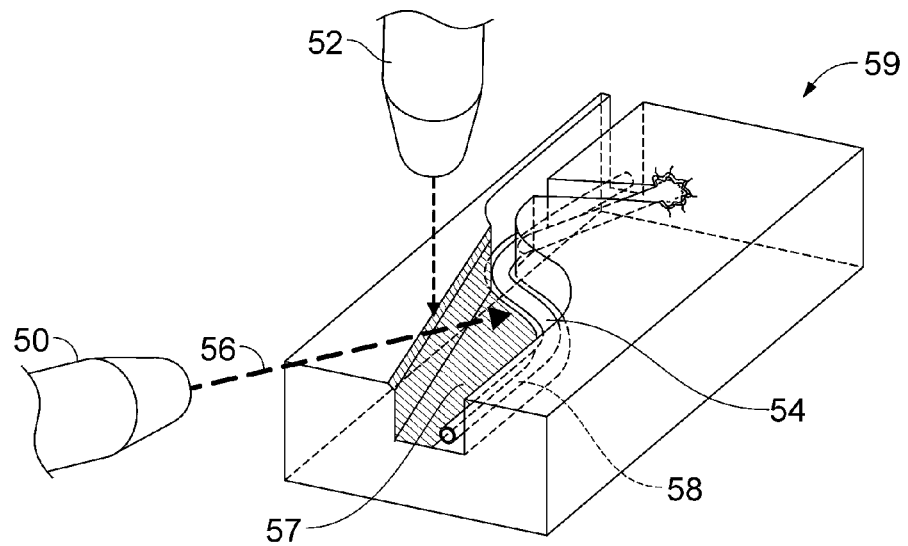
FIG. 5B shows the obstruction portion of the sample removed to allow imaging of the feature by the SEM.

As illustrated in FIG. 5A the beam 56 of the SEM 50 is unable to impinge on portion 54 of the feature 58. Here, the FIB 52 is directed to obliterate obstruction 57 of the sample 59. FIG. 5B shows the sample 59 with obstruction 57 removed, and SEM beam 56 with a direct line-of-sight to portion 54 of the feature 58.

Preferably, this obliteration process can be performed with a faster, less precise milling procedure so that the obstructing sample material is quickly removed. In this rough milling, the FIB operating parameters are preferably between 21 nA-6.5 nA depending on the size of the obstruction and its material composition.

A problem that may occur while milling the remnant with a faster milling procedure is redeposition. That is, particles of the remnant material may redeposit on the face of the feature to be imaged, causing an undesirable image resolution should the face with redeposited material be imaged. Here, a clean up step may be performed before imaging the face. The clean up step preferably includes directing a higher quality beam toward the face the ion beam with than that used to obliterate the remnant material. The FIB current settings for the clean-up step are preferably between 2.8 nA-500 pA, depending on feature size and material.

Alternatively, it may be predetermined that a subsequent slice milling procedure will cause a sample material obstruction between the SEM and the new face. In this case, the sample material obstruction, or remnant, may be preventatively obliterated before the subsequent new face is milled, thereby preventing a separate clean-up step.

Figure 6:
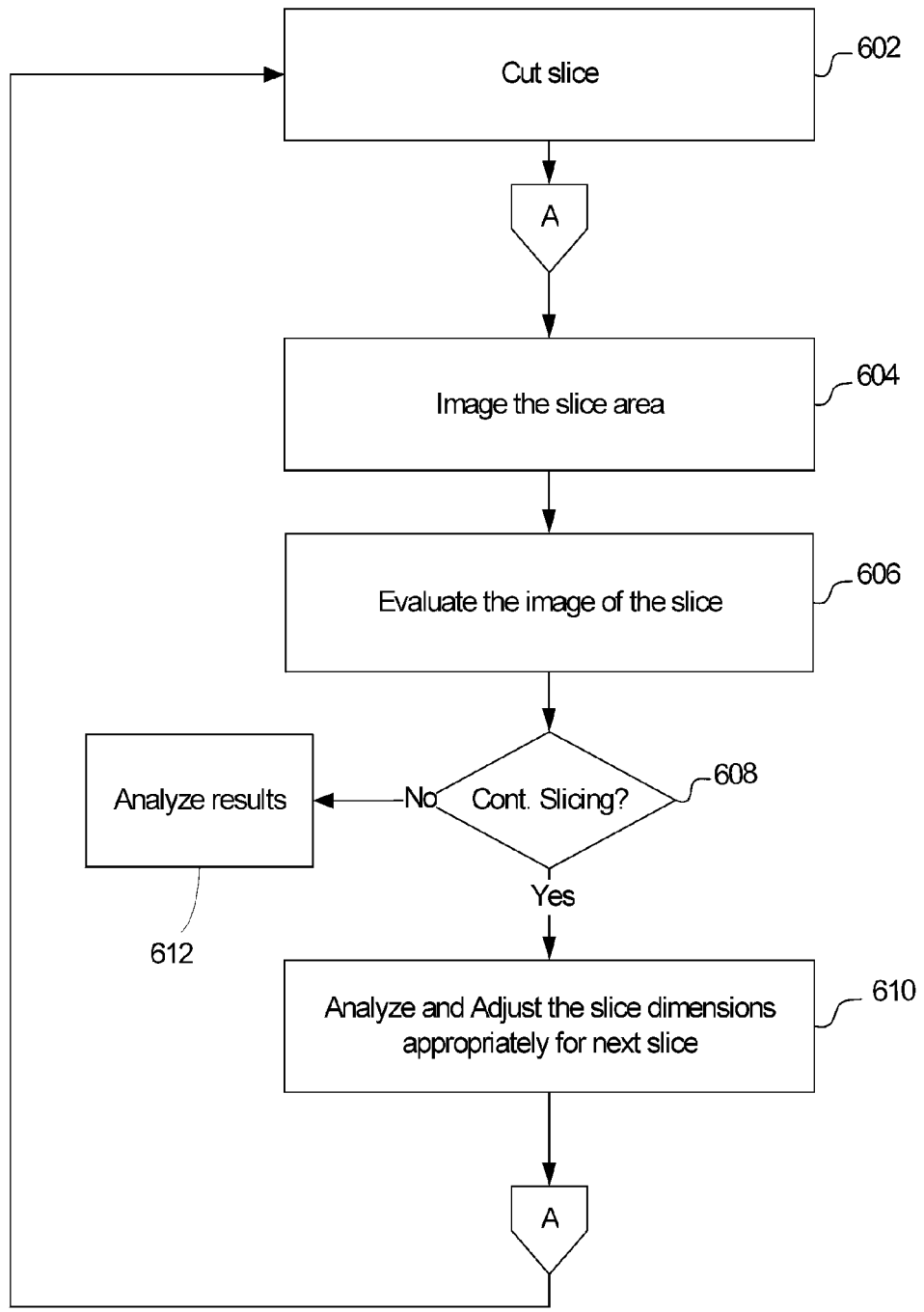
FIG. 6 is a flow chart showing the steps of preferred embodiments of the present invention, with parallelogram "A" leading to FIG. 7.
Figure 7:
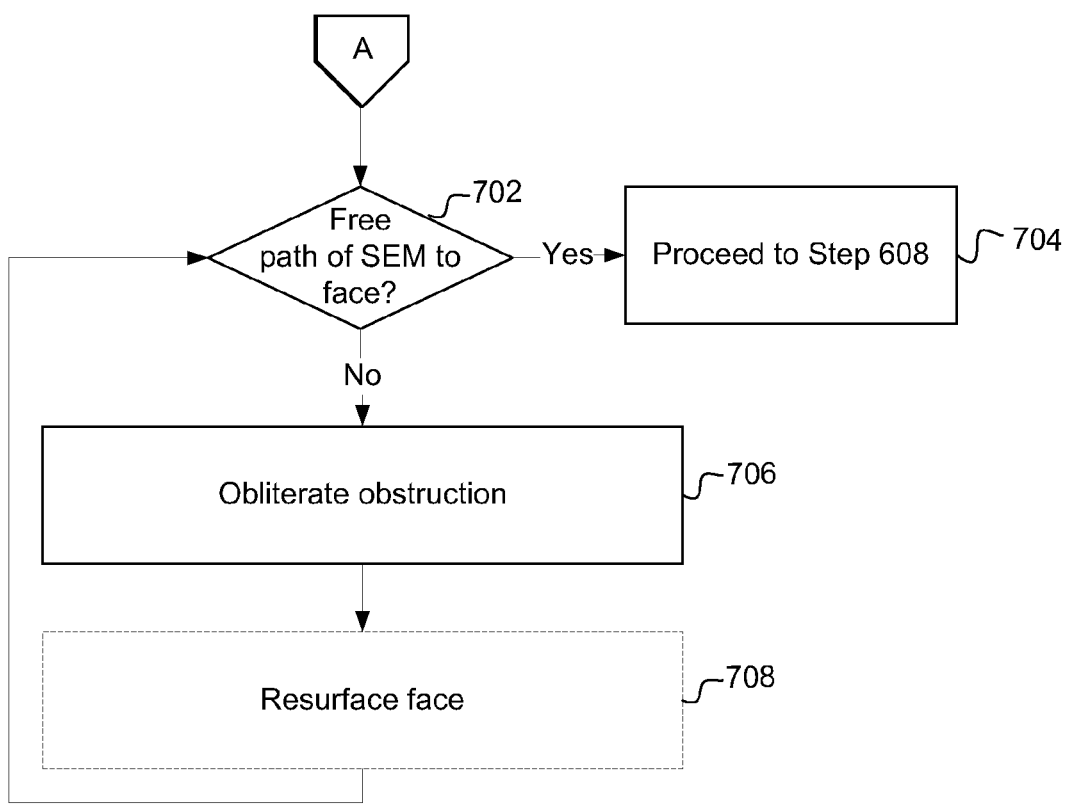
FIG. 7 is a flow chart showing additional steps of FIG. 6 by following parallelogram "A" of FIG. 6.

FIGS. 6 and 7 (with parallelogram "A" of FIG. 6 leading to FIG. 7) are flow charts showing preferable steps of a method in accordance with embodiments of the present invention. The steps of preferred embodiments as illustrated in the figures broadly include slicing-and-imaging steps, locating the feature of interest with machine vision, evaluating and measuring of the feature in the resulting image, and adjustment of the dual beam system for continued processing according to the results of the evaluation step.

In operation, the sample is loaded into an imaging system such as the DA-300 Defect Analyzer or the Helios NanoLab 400 DualBeam tool from FEI Company. In step 602, a slice is cut into the sample perpendicularly to the sample's upper surface to create a milled face area. If this is the first slice into the sample, it is an initial slice and may be different than subsequent slices in that the location of the feature of interest may not be known with a desired level of certainty. If it is predetermined that the location of the feature of interest in an initial image will not be accurately determinable before an initial slice, it is preferable that a large initial slice be performed in order to locate the feature of interest in a resulting image of that area. If the location of the feature of interest will be known with a high level of certainty, a relatively smaller slice may be made in order to save time.

By following parallelogram "A" of FIG. 6 which leads to FIG. 7, it is determined in step 702 whether a free and clear path of the SEM exists to image the slice face. If there is not a free path, as is common after an initial slice or after further processing as described below, the obstruction is obliterated in step 706. As discussed above, obliterating an obstruction may cause redeposition of sample material onto the freshly cut face. In this case, the face is resurfaced in step 708. Alternatively, a portion of the sample material that is predetermined to be an obstruction to the SEM can be preemptively removed before an initial face is made. If there is a free path of the SEM to the slice face, step 704 returns the process to step 608 of FIG. 6.

After creating a face and removing any obstruction to the SEM, an image of the slice area can then be obtained by the SEM in step 604. In step 606, the image is evaluated to locate and measure the feature of interest. The evaluation step preferably includes evaluation of the image by software operating on a computer associated with the machine vision or other program, or it may be evaluated by a human operator. It is preferable that the evaluation is computerized, however, so that it may be automated to quickly evaluate (e.g. locate and measure) the feature in each image of the slice and view process. As discussed above, preferable ways of locating and measuring a feature include contrast comparison for edge detection and center-of-mass detection. If performed manually, for example, the center of mass can be indicated by an operator using a computer mouse, stylus or equivalent means on a computer image or display.

After the image is evaluated, it is determined if slicing should continue in step 608. To rebuild a 3D image of a feature through this technique, it is desirable to obtain many images, depending on the size of the feature or the desired 3D detail. This step allows for counting the iterations of the slice and view technique as it processes the feature in the sample. The process may continue until a predetermined number of slices have been performed, or it may, at some trigger event or after so many iterations, require other input rather than merely number counting to determine if processing should continue. In any case, if it is determined that the reiterative slicing process has concluded, the flow follows the "No" path to analyze the results of the images in step 612. In this step, the images are typically processed to reconstruct the feature into a 3D image. The 3D image is then typically analyzed by manual operators. Software for 3-D construction may preferably include, for example, Amira three dimensional imaging software from Visage Imaging, Inc. San Diego, Calif., or Avizo three-dimensional visualization software from VSG, Visualization Sciences Group, Inc. Burlington, Mass. If it is determined that reiterative slicing processes should continue, the flow follows the "Yes" path to step 610.

In step 610, the image of the feature and the information from the evaluation step of 606 is analyzed as to whether to change system, or beam, parameters for the subsequent slice and view steps 602 and 604. To this end, a bounding box that encompasses the feature is useful. The bounding box is preferably assigned to the image in the evaluation step 606 or the previous adjustment step 610 of the previous iteration of these steps (i.e. if this is not the initial execution of this step in this process). As described above, the bounding box surrounding the feature is preferably extends beyond the edges of the feature by a nominal amount to account for the possibility of a growing feature in the next image.

A change in the size and location of the bounding box dictates a change in the parameters of the beams and the location to which they are directed in the subsequent iteration of the slice and view process. That is, the X and Y dimensions of the area to slice and view are changed for the following slice and view iteration with respect to a change in the bounding box dimensions. For example, if the feature size and shape change significantly, the bounding box dimensions are adjusted and the beams are adjusted accordingly to slice and view the next face. If the feature dimensions decrease, the bounding box dimensions are adjusted (reduced in one or more of the X and Y dimensions) so that the FIB is adjusted to make a smaller area slice, therefore requiring less time to slice and view. If the bounding box size increases, the beams will slice and view a larger area of the substrate. In either case, the beams are adjusted to slice and view an area of the substrate that includes the feature of interest and a minimal area around the feature. To this end, it is preferable that the width (X-dimension) of the bounding box be less than 300% the width (X-dimension) of the feature of interest, more preferable that the width of the bounding box be less than 200% the width of the feature of interest, and even more preferable that the width of the bounding box be less than 150% the width of the feature of interest. And if the feature position or location changes with respect to the previous image of the feature, the beams are directed in that location accordingly. It is also preferable that in addition to, or in place of, adjusting the area to be slice milled, the sample may be repositioned in relation to the beams, as described above with respect to the embodiment illustrated in FIG. 4A.

After adjusting (if required) the location and area of the sample to be milled and imaged, or repositioning the sample, the process flows back to step 602 to reiterate the process. However, before proceeding to step 602, it is preferable to determine if proceeding with the next slice will cause an obstruction to imaging with the SEM. Here the process flows through parallelogram "A" and follows the steps of FIG. 7 as discussed above.

Figure 8:
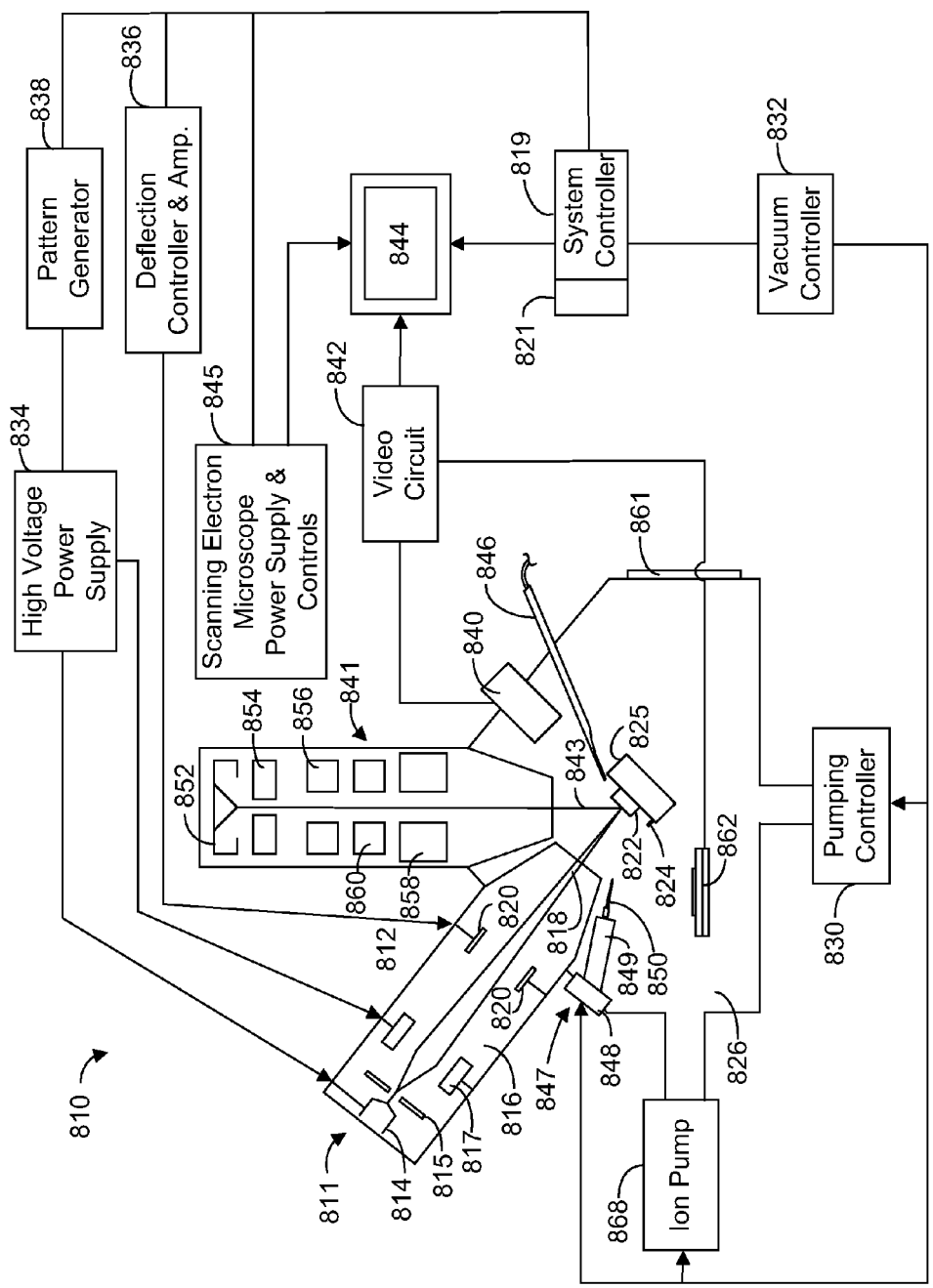
FIG. 8 shows a typical dual beam system used to implement the present invention.

A preferred apparatus for performing the preferred embodiments of the methods described above is shown in FIG. 8, illustrating a typical dual beam system 810 with a vertically mounted SEM column and a focused ion beam (FIB) column mounted at an angle of approximately 52 degrees from the vertical. Such dual beam systems are commercially available, for example, from FEI Company, Hillsboro, Oreg., the assignee of the present application. While an example of suitable hardware is provided below, the invention is not limited to being implemented in any particular type of hardware.

A scanning electron microscope 841, along with power supply and control unit 845, is provided with the dual beam system 810. An electron beam 843 is emitted from a cathode 852 by applying voltage between cathode 852 and an anode 854. Electron beam 843 is focused to a fine spot by means of a condensing lens 856 and an objective lens 858. Electron beam 843 is scanned two-dimensionally on the specimen by means of a deflection coil 860. Operation of condensing lens 856, objective lens 858, and deflection coil 860 is controlled by power supply and control unit 845.

Electron beam 843 can be focused onto substrate 822, which is on movable X-Y stage 825 within lower chamber 826. When the electrons in the electron beam strike substrate 822, secondary electrons are emitted. These secondary electrons are detected by secondary electron detector 840 as discussed below. STEM detector 862, located beneath the TEM sample holder 824 and the stage 825, can collect electrons that are transmitted through the sample mounted on the TEM sample holder as discussed above.

Dual beam system 810 also includes focused ion beam (FIB) system 811 which comprises an evacuated chamber having an upper neck portion 812 within which are located an ion source 814 and a focusing column 816 including extractor electrodes and an electrostatic optical system. The axis of focusing column 816 is tilted 52 degrees from the axis of the electron column. The ion column 812 includes an ion source 814, an extraction electrode 815, a focusing element 817, deflection elements 820, and a focused ion beam 818. Ion beam 818 passes from ion source 814 through column 816 and between electrostatic deflection means schematically indicated at 820 toward substrate 822, which comprises, for example, a semiconductor device positioned on movable X-Y stage 825 within lower chamber 826.

Stage 825 may also support one or more TEM sample holders 824 so that a sample can be extracted from the semiconductor device and moved to a TEM sample holder. Stage 825 can preferably move in a horizontal plane (X and Y axes) and vertically (Z axis). Stage 825 can also tilt approximately sixty (60) degrees and rotate about the Z axis. In some embodiments, a separate TEM sample stage (not shown) can be used. Such a TEM sample stage will also preferably be moveable in the X, Y, and Z axes. A door 861 is opened for inserting substrate 822 onto X-Y stage 825 and also for servicing an internal gas supply reservoir, if one is used. The door is interlocked so that it cannot be opened if the system is under vacuum.

An ion pump 828 is employed for evacuating neck portion 812. The chamber 826 is evacuated with turbomolecular and mechanical pumping system 830 under the control of vacuum controller 832. The vacuum system provides within chamber 826 a vacuum of between approximately $1 \times 10^{-7}$ Torr and $5 \times 10^{-4}$ Torr. If an etch assisting, an etch retarding gas, or a deposition precursor gas is used, the chamber background pressure may rise, typically to about $1 \times 10^{-5}$ Torr.

The high voltage power supply provides an appropriate acceleration voltage to electrodes in ion beam focusing column focusing 816 for energizing and focusing ion beam 818. When it strikes substrate 822, material is sputtered, that is physically ejected, from the sample. Alternatively, ion beam 818 can decompose a precursor gas to deposit a material.

High voltage power supply 834 is connected to liquid metal ion source 814 as well as to appropriate electrodes in ion beam focusing column 816 for forming an approximately 1 keV to 60 keV ion beam 818 and directing the same toward a sample. Deflection controller and amplifier 836, operated in accordance with a prescribed pattern provided by pattern generator 838, is coupled to deflection plates 820 whereby ion beam 818 may be controlled manually or automatically to trace out a corresponding pattern on the upper surface of substrate 822. In some systems the deflection plates are placed before the final lens, as is well known in the art. Beam blanking electrodes (not shown) within ion beam focusing column 816 cause ion beam 818 to impact onto blanking aperture (not shown) instead of substrate 822 when a blanking controller (not shown) applies a blanking voltage to the blanking electrode.

The liquid metal ion source 814 typically provides a metal ion beam of gallium. The source typically is capable of being focused into a sub one-tenth micrometer wide beam at substrate 822 for either modifying the substrate 822 by ion milling, enhanced etch, material deposition, or for the purpose of imaging the substrate 822.

A charged particle detector 840, such as an Everhart Thornley or multi-channel plate, used for detecting secondary ion or electron emission is connected to a video circuit 842 that supplies drive signals to video monitor 844 and receiving deflection signals from a system controller 819. The location of charged particle detector 840 within lower chamber 826 can vary in different embodiments. For example, a charged particle detector 840 can be coaxial with the ion beam and include a hole for allowing the ion beam to pass. In other embodiments, secondary particles can be collected through a final lens and then diverted off axis for collection.

A micromanipulator 847, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 847 may comprise precision electric motors 848 positioned outside the vacuum chamber to provide X, Y, Z, and theta control of a portion 849 positioned within the vacuum chamber. The micromanipulator 847 can be fitted with different end effectors for manipulating small objects. In the embodiments described herein, the end effector is a thin probe 850.

A gas delivery system 846 extends into lower chamber 826 for introducing and directing a gaseous vapor toward substrate 822. U.S. Pat. No. 5,851,413 to Casella et al. for "Gas Delivery Systems for Particle Beam Processing," assigned to the assignee of the present invention, describes a suitable gas delivery system 846. Another gas delivery system is described in U.S. Pat. No. 5,435,850 to Rasmussen for a "Gas Injection System," also assigned to the assignee of the present invention. For example, iodine can be delivered to enhance etching, or a metal organic compound can be delivered to deposit a metal.

System controller 819 controls the operations of the various parts of dual beam system 810. Through system controller 819, a user can cause ion beam 818 or electron beam 843 to be scanned in a desired manner through commands entered into a conventional user interface (not shown). Alternatively, system controller 819 may control dual beam system 810 in accordance with programmed instructions stored in a memory 821. In some embodiments, dual beam system 810 incorporates image recognition software, or machine vision, as discussed above.

Experimental Example

An example of preferable FIB parameters for a performing a preferred embodiment of the present invention on a typical biological sample include rough milling beam current setting at 21 nA, clean up milling current setting at 2.8 nA, slice milling current setting at 460 pA. Preferable SEM parameters include beam acceleration voltage of 1 kV and current of 170 pA.

During an experiment performed with these system settings, back scattered electron (BSE) images were collected with contrast and brightness values digitally inverted, and image horizontal field width (HFW) of 25 µm. Slice thickness was 30 nm and 200-300 slices were processed for a completion time of 6-8 hours.

Although embodiments of the present invention and its advantages have been described in detail, it should be understood that various changes, substitutions and alterations can be made herein without departing from the spirit and scope of the invention as defined by the appended claims. For example, while the examples provided show the use of the invention in connection with a typical slice and view procedure, alternative implementations of the method and apparatus described here may use a laser for rough milling and e-beam chemistry for thin slicing. Also, it is considered within the scope of the invention that the angle between the FIB and the SEM can be other than 52 degrees, such as 45-54 degrees, for example. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

I claim as follows:

1. A method for observing a feature within a substrate using charged particle beam imaging, comprising:
   (a) directing an ion beam toward the substrate to expose a cross section including the feature;
   (b) directing a charged particle beam toward the cross section to obtain image information about the cross section;
   (c) analyzing the image information of the feature to determine parameters for carrying out an exposing of a subsequent cross section, the subsequent cross section including the feature, wherein the parameters include a size and shape of an area to be milled, a position of the substrate relative to the ion beam and the charged particle beam, or a combination thereof; and
   (d) carrying out the exposing of the subsequent cross section.

2. The method of claim 1, wherein the charged particle beam comprises an electron beam.

3. The method of claim 1, wherein the charged particle beam comprises an ion beam.

4. The method of claim 1, in which analyzing the image information of the feature to determine parameters for carrying out an exposing of a subsequent cross section includes finding a bounding box that bounds the feature.

5. The method of claim 1, further comprising adjusting the position of the substrate based on the analysis of the image information to acquire a cross-section of the feature in which the cross-section is perpendicular to a longitudinal axis of the feature.

6. The method of claim 2, further comprising:
   a) determining if an obstruction exists that obstructs a path of the electron beam to the cross section including the feature; and
   b) obliterating the obstruction if it exists.

7. The method of claim 6, further comprising resurfacing an area of the cross section to remove redeposited substrate material.

8. A memory device comprising computer-executable instructions, wherein the computer-executable instructions, when executed, cause a charged particle beam imaging system to:
   obtain image information about a region of a sample by scanning the region with a charged particle beam;
   locate a feature in the sample using the image information;
   obtain measurements of physical properties of the feature by processing the image information; and
   use the measurements to determine parameters for carrying out an exposing of a cross section of the sample with an ion beam, wherein the cross section of the sample includes a cross section of the feature and the parameters include a size and shape of an area to be milled, a position of the sample relative to the ion beam and the charged particle beam, or a combination thereof.

9. The memory device of claim 8, wherein the instructions, when executed, cause the charged particle beam imaging system to expose the cross section of the sample with the ion beam.

10. The memory device of claim 8, wherein the charged particle beam comprises an electron beam.

11. The memory device of claim 8, wherein the charged particle beam is the ion beam.

12. The memory device of claim 8, wherein the computer-executable instructions, when executed, cause the charged particle beam imaging system to determine a contrast, a gray level, edge boundaries and/or a texture of the feature in relation to material of the sample surrounding the feature.

13. The memory device of claim 8, wherein the instructions, when executed, cause the charged particle beam imaging system to locate the feature by using machine vision to identify the feature.

14. The memory device of claim 8, wherein the computer instructions, when executed, cause the charged particle beam imaging system to:
   process the image information to obtain a location of the feature; and
   use the measurements and the location to determine the parameters for carrying out the exposing of the cross section of the sample.

15. The memory device of claim 14, wherein using the measurements and the location to determine the parameters for carrying out the exposing of the cross section of the sample includes predicting a location, a size, and a shape of the feature in the cross section based on the location of the feature and the measurements of the physical properties of the feature obtained by processing the image information.

16. The memory device of claim 14, wherein using the measurements and the location to determine the parameters for carrying out the exposing of the cross section of the sample includes predicting a location of the feature in the cross section based on the location of the feature and the measurements of the physical properties of the feature obtained by processing the image information.

17. A system for observing a feature within a substrate using charged particle beam imaging, including:
   an ion beam column for generating, focusing, and directing an ion beam;
   an electron beam column for generating, focusing, and directing an electron beam; and
   a memory including stored computer instructions,
   wherein the computer instructions, when executed, cause the system to:
   (a) expose a cross section of the feature to be observed by slice milling the substrate using the ion beam;
   (b) direct the electron beam toward the exposed cross section to obtain image information of the feature;
   (c) process the image information to locate and obtain measurements of physical properties of the feature;
   (d) use the measurements to determine parameters for carrying out a subsequent slice milling to expose a subsequent cross section of the feature, wherein the parameters include a size and shape of an area to be milled, a position of the substrate relative to the ion beam and the electron beam, or a combination thereof;

(e) carry out the subsequent slice milling using the ion beam; and (f) repeat steps (a) through (c).

18. The system of claim 17, further comprising a controller for controlling an operation of parts of the system in accordance with the computer instructions.

19. The system of claim 17, wherein processing the image information comprises using machine vision to obtain the measurements of the physical properties of the feature.

20. The system of claim 17, wherein the computer instructions, when executed, cause the system to:

process the image information to obtain a location of the feature; and use the measurements and the location to determine the parameters for carrying out the subsequent slice milling.

21. The system of claim 20, wherein using the measurements and the location to determine the parameters for carrying out the subsequent slice milling to expose the subsequent cross section includes predicting a location, a size, and a shape of the feature in the subsequent cross section based on the location of the feature and the measurements of the physical properties of the feature obtained by processing the image information.

* * * * *